United States Patent [19]

Pluim, Jr.

[11] Patent Number: 4,803,047

[45] Date of Patent: * Feb. 7, 1989

[54] METHOD FOR NEUTRALIZING OFFENSIVE CHEMICALS

[76] Inventor: Arthur W. Pluim, Jr., 324 E. Hazel, Stillwater, Minn. 55082

[*] Notice: The portion of the term of this patent subsequent to Jun. 10, 2003 has been disclaimed.

[21] Appl. No.: 54,960

[22] Filed: May 28, 1987

Related U.S. Application Data

[63] Continuation-in-part of Ser. No. 870,639, Jun. 4, 1986, which is a continuation-in-part of Ser. No. 589,595, Mar. 14, 1984, Pat. No. 4,594,239.

[51] Int. Cl.$^4$ .......................... A61L 9/01; A61K 7/135
[52] U.S. Cl. ............................................. 422/5; 424/10
[58] Field of Search .............................. 422/5; 424/10

[56] References Cited

U.S. PATENT DOCUMENTS

| | | | |
|---|---|---|---|
| 2,630,399 | 5/1953 | Sulzberger et al. | 514/392 |
| 2,725,335 | 11/1955 | Lazier | 424/10 |
| 2,885,305 | 5/1959 | Speck | 424/27 |
| 3,003,971 | 10/1961 | Prichard | 548/304 |
| 3,749,772 | 7/1973 | Cardelli et al. | 424/81 |
| 3,756,976 | 9/1973 | Uraneck | 524/836 |
| 3,930,005 | 12/1975 | Woinan et al. | 424/253 |
| 4,259,318 | 3/1981 | Duhe et al. | 424/94 |
| 4,283,373 | 8/1981 | Frech et al. | 423/226 |
| 4,594,239 | 6/1986 | Pluim | 422/5 |

*Primary Examiner*—Barry S. Richman
*Assistant Examiner*—Lyle Alfandary Alexander
*Attorney, Agent, or Firm*—Dean P. Edmundson

[57] ABSTRACT

A method is described for neutralizing urushiol on surfaces (e.g., wearing apparel, skin, tools, pets, etc.) with an aqueous solution comprising a water-soluble chlorine-containing compound which is a stable solid at room temperature. The solutions are also useful for deodorizing low molecular weight thiols such as are present in skunk spray or glandular secretions of other small animals. Because the chlorine-containing compounds are stable solids, they can be shipped and stored in solid form and dissolved in water at the time of use.

10 Claims, No Drawings

METHOD FOR NEUTRALIZING OFFENSIVE CHEMICALS

CROSS-REFERENCE TO RELATED APPLICATION

This application is a continuation-in-part of my co-pending application Ser. No. 06/870,639, filed June 4, 1986, which is a continuation-in-part of my earlier filed application Ser. No. 06/589,595, filed Mar. 14, 1984, now U.S. Pat. No. 4,594,239, issued June 10, 1986.

FIELD OF THE INVENTION

This invention relates to methods and techniques for neutralizing or detoxifying offensive chemicals. More particularly, this invention relates to neutralizing the toxin urushiol which is present in members of the botanical family Anacardiaceae (e.g., poison ivy, poison oak, poison sumac, cashew, etc.). The invention also relates to the deodorizing of low molecular weight thiols.

BACKGROUND OF THE INVENTION

The irritating nature of poison ivy sap was first recorded in 1609 by Captain John Smith after his arrival in North America. Since that time many compounds and practices have been tried unsuccessfully to mitigate, render harmless, or destroy, the toxic principle of the dermatogenic members of the botanical family Anacardiaceae. The members, which include poison ivy, poison oak, poison sumac, the lacquer tree, mango and cashew, belong to an immunologic cross reacting group which have biochemically similar antigens. The antigens are 1,2 dihydroxy-benzenes with a 15 or 17 carbon atom aliphatic side chain which has varying degrees of unsaturation. It is not unusual for the sap of different plants to have mixtures of dihydroxy benzenes or to have these compounds in common but at different concentration levels.

The allergic contact dermatitis is reported in the literature to be caused by the catechol moiety as the primary allergen. The aliphatic hydrocarbon side group allows bonding to and penetration of the skin.

Exposure of skin to urushiol, after a time, results in a painful rash or itching at the area of contact which often proceeds to vesicles. The dermatological reaction may require a month or more to heal.

Bare skin contact with the urushiol is a prerequisite for the allergic reaction. However, direct contact with the plant sap by bare skin is not necessary and often is not the primary contamination surface. In fact, there are many vectors responsible for the spread of the urushiol; for example, clothing, tools, and domestic animals, and even the fingers spread the urushiol to other parts of the body. Failure to appreciate an exposed article as a carrier is responsible for most personal exposure. Evading this secondary contamination from exposed articles is difficult because of the small amount of the urushiol needed to cause the allergic reaction as well as the relatively unobtrusive evidence of its presence. Furthermore, even if exposure of skin or articles were noted, this most often would occur in the field where there is usually no access to relief, such as clean clothes or the ability to scrub with soap and water. Additionally, contaminated articles can retain allergic reaction-causing capabilities for up to one year after the original exposure because of the refractory nature of the urushiol oleoresin.

It might seem relatively easy to destroy the urushiol since the catechol moiety is a strong reducing agent and might be expected to react readily with strong oxidizing agents to accomplish its destruction. This is the case when acidic, aqueous solutions of strong oxidizers such as permanganates, peroxides, or chlorites effectively destroy the catechol as the water soluble pyrocatechol. However, these same oxidizing agents will not destroy the hydrophobic catechol moiety as presented in the urushiol.

Exposure to skunk spray is a great annoyance because of its very disagreeable and persistent odor due to the low molecular weight thiols. The odor may persist for several days on anything contacted by the spray, e.g., wearing apparel, pets, articles, etc. In particular, dogs are often exposed to the spray and become a nuisance when attempts are made to decontaminate them, restrain them, etc.

Because the skunk spray is quite hydrophobic, removal of the spray and the primary odor-causing factors (n-butanethiol and 2-methylbutanethiol) by ordinary means such as soap and water is very difficult. Soaking exposed articles in tomato juice or perfumed detergents for extended periods have been suggested but have not proven particularly effective.

It has also been suggested that thiols can be deodorized by oxidizing them to the disulfides. This is common practice in the sweetening of sour natural gas or crude oil. However, such processes involve the use of catalysts and high temperatures and are performed in continuous flow reactors under controlled conditions.

SUMMARY OF THE INVENTION

In accordance with the present invention techniques are described for effectively neutralizing urushiol on a surface (e.g., wearing apparel, skin, tools, pets, etc.) The techniques include contacting the urushiol with an aqueous solution comprising a water-soluble chlorine-containing compound which is a stable solid at room temperature and which is capable of reacting with urushiol to produce non-allergic reaction products.

Using the techniques of this invention, urushiol on exposed surfaces is destroyed so that secondary contamination is avoided quickly and efficiently.

In another aspect of the invention it has been found that the chlorine-containing compounds are also effective in deodorizing low molecular weight thills such as are present in skunk spray or glandular secretions of other small animals. Thus, the technique is effective for eliminating the offensive odor of skunk spray, etc. from wearing apparel, pets and so forth.

DETAILED DESCRIPTION OF THE INVENTION

In the description of this invention the term "urushiol" is used to generically include any dermatogenic 1,2-dihydroxy benzene with a 15 or 17 carbon atom side chain in the 3 position on the benzene ring. The reference herein to a "surface" refers normally to the upper or exterior bounds of an object which may have come into contact with the sap and toxic principle of the dermatogenic members of the botanical family Anacardiaceae. Examples of such surfaces include wearing apparel (e.g., clothing, shoes, boots), skin, animal hair, tools, toys, etc.

The chlorine-containing compounds which have been found useful in the techniques of the present invention may be inorganic or organic. The useful compounds are water-soluble and are stable solids at room temperature.

Preferred chlorine-containing compounds for use in this invention are water-soluble chloramine compounds. In particular, the alkali metal salts of dichloroisocyanuric acid are very useful. These compounds are stable in solid form at room temperature. They can be shipped and stored as such and then dissolved in water at the time of use. This provides significant economic and functional benefits.

The preferred compounds include: sodium dichloroisocyanurate, sodium dichloroisocyanurate dihydrate, and potassium dichloroisocyanurate. Other useful chloramines which are stable solids and which are substantially water soluble are chloramine T and chloramine B.

There are also other chlorine-containing compounds which are stable in the solid state which, although they could be used in the practice of the invention, are not preferred. These compounds are calcium hypochlorite and its derivatives, lithium hypochlorite, and chlorinated trisodium phosphate dodecahydrate. Other chlorinated lime products could also be used, such as tropical bleach (25-30% available chlorine), semi-tropical bleach (33-35% available chlorine), and bleaching powder (35-37% available chlorine). Some of these materials are more expensive than the preferred compounds, and some of these materials may leave sludges and residues which may be irritating or otherwise objectionable.

Normally, in order to be stable for useful lengths of time, hypochlorite solutions are made up in relatively low concentrations and stabilized with strong alkalies. It has been discovered that these salts, because their solutions are prepared for more or less immediate use, can be made in a sufficiently stronger concentration so as not to require presence of alkali to be operational. Reduction or elimination of alkalinity is of great importance when the methods of the invention are practiced on the skin or in the event of eye contact to prevent irritation or tissue damage. Alkalies may optionally be included to prepare more active solutions. These alkalies can be, for example, the sodium or potassium bicarbonates, carbonates or hydroxides.

All of the foregoing compounds, when dissolved in water, are effective in destroying or neutralizing urushiol on exposed surfaces (e.g., wearing apparel, tools, etc.). In this manner secondary exposure to urushiol contact is eliminated or avoided.

The aqueous solutions of the chlorine-containing compounds preferably have a concentration of about 5 to about 25% by weight. Below a concentration of about 5% the solution does not always neutralize all of the urushiol. At about 25% the upper limits of solubility of the compounds in water is reached. The aqueous solutions are particularly useful for treatment of surfaces which might be adversely affected by organic solvents. Alkali may optionally be included to serve as an indicator which shows the presence of urushiol by producing a green color (which fades coincident with the destruction of the urushiol). This alkali is normally sodium or potassium hydroxide. If desired, there also may be added to the aqueous solution small amounts of a conventional wetting agents.

A typical, preferred formulation for use in the present invention is a 5% by weight solution of sodium dichloroisocyanurate in water. One commercially available source of this compound is ACL 60 from Monsanto.

Additionally, a means of indicating the presence and subsequent destruction of the urushiol can be employed by dissolving a ferric salt in the aqueous solutions described herein. Such ferric salts include, for example, ferric nitrate, ferric chloride, ferric ammonium citrate or ferric acetate.

Besides the decontamination of clothing, shoes, gloves, tools and other articles it is desirable to directly treat human or animal skin. When human skin is the primary surface which has been contacted by urushiol there is a time constraint in which to neutralize or destroy the urushiol. After initial skin contact by urushiol, there is an induction period of 15-30 minutes. If the exposed skin surface is cleansed or treated during the induction period to remove or destroy the urushiol, then the typical allergic response is averted. Consequently, the chemical cleansing or decontamination should work quickly, preferably in less than 5 minutes. Also, since the decontamination means is being applied directly to the skin, a low order of dermal toxicity is required. The solutions of chlorine-containing compounds used in this invention exhibit low dermal response. This allows their use on pets and other domestic animals which are sometimes carriers of urushiol contamination.

An example of the use of the chemical decontamination means on the human skin is as follows: Zones, approximately 2.5 cm in diameter, are marked on the forearm of a human subject. Each zone is treated with 2-5 drops of a 1½% catechol solution in water. At intervals of 5, 10, 15, 20, and 30 minutes, different zones are treated with a 5% aqueous solution of the invention. A control zone is left untreated. After removing excess fluid with a paper towel, the sites are left undisturbed for 2 minutes. At that time a pad saturated with 20% by weight ferric nitrate aqueous solution is daubed across the experimental area and reactions are observed. The control zone turns black from the catechol-ferric ion reaction. The zones treated with an aqueous solution of the invention show various responses: the zones treated at the 5 and 10 minutes intervals do not show any black color indicative of contact appearing as undisturbed skin; the zone treated at the 15 minute interval has a slight bit of color indicative of some binding to the skin. The sites treated at the 20 and 30 minute intervals are only slightly less dark than the control zone. No reddening or other sign of skin irritation is noted. Thus, the decontamination means is operable within the required time frame.

The compositions useful in the present invention can be delivered to the desired surface to be decontaminated by any practical means including but not limited to aerosol sprays, pump sprays, wipes, swabs, immersion, sprinkling and the like. Thus, the present invention comprises a chemical means for deactivating, destroying or otherwise rendering harmless the toxic principle, urushiol, found in the sap of poison ivy, poison oak, poison sumac and related plans of the botanical family Anacardiaceae, on surfaces exposed to same. It comprises a chlorine containing compound in a suitable carrier. This means is operable on surfaces as exposed, and in the field environment is necessary.

In another aspect the present invention provides means for deodorizing low molecular weight thiols, such as those present in skunk spray and in glandular secretions of other small animals such as cats, ferrets, etc. Exposure to skunk spray is a great annoyance because of it its very disagreeable and persistent odor due to the low molecular weight thiols. The odor may persist for several days on anything contacted by the spray, e.g., wearing apparel, pets, articles, etc. In particular, dogs are often exposed to the spray and become a nuisance when attempts are made to decontaminate them, restrain them, etc.

Because the skunk spray is quite hydrophobic, removal of the spray and the primary odor-causing factors (n-butanethiol and 2-methylbutanethiol) by ordinary means such as soap and water is very difficult. Soaking exposed articles in tomato juice or perfumed detergents for extended periods have been suggested but have not proven effective.

It has also been suggested that thiols can be deodorized by oxidizing them to the disulfides. This is common practice in the sweetening of sour natural gas. However, such processes involve the use of catalysts and high temperatures and are performed in continuous flow reactors under control conditions.

It has been found that the compositions described above in connection with the neutralization of urushiol also have utility in oxidizing low molecular weight thiols to thereby deodorize them. The compositions described above are effective in deodorizing the thiols despite the hydrophobic nature thereof.

In the description of this invention the term "low molecular weight thiols" includes thiols which have a boiling point less than about 100° C. For example, this includes thiols such as methanethiol, ethanethiol, 1-propanethiol, 2-propanethiol, 2-methyl-1-propanethiol, 2-methyl-2-propanethiol, n-butanethiol, and 2-methylbutanethiol. The reference herein to a "surface" refers normally to the upper or exterior bounds of an object which may have come into contact with a low molecular weight thiol. Examples of such surfaces include wearing apparel (e.g., clothing, shoes, boots), skin, animal hair, tools, toys, automobiles, lawns, furniture, carpeting, etc.

Thus, these compounds are effective in neutralizing or deodorizing low molecular weight thiols on exposed surfaces (e.g., wearing apparel, tools, etc.). These compounds are effective in neutralizing (i.e., deodorizing) low molecular weight thiols such as are present, for example, in skunk spray, in glandular secretions of other small animals such as cats, ferrets, and so forth, various lures (e.g., "Buck Stop Skunk Scent"), as well as other natural or synthetic thiols.

Other variants of the invention are also possible without departing from the scope and spirit of the present invention.

What is claimed is:

1. A method for decontaminating a surface which has been exposed to a urushiol, said method being for the purpose of neutralizing said urushiol, wherein said method comprises contacting said urushiol with an effective amount of an aqueous solution of a chlorine-containing compound which is capable of reacting with said urushiol to produce non-allergic reaction products, wherein said chlorine-containing compound is a water-soluble compound which is a stable solid at room temperature.

2. A method in accordance with claim 1, wherein said chlorine-containing compound is selected from a group consisting of sodium dichloroisocyanurate, sodium dichloroisocyanurate dihydrate, and potassium dichloroisocyanurate.

3. A method in accordance with claim 1, wherein said chlorine-containing compound is selected from a group consisting of calcium hypochlorite, hemibasic calcium hypochlorite, lithium hypochlorite, and chlorinated trisodium phosphate dodecahydrate.

4. A method in accordance with claim 1, wherein said surface comprises wearing apparel.

5. A method in accordance with claim 1, wherein said solution is applied to said surface by spraying, wiping, or immersion.

6. A method in accordance with claim 1, wherein said solution further comprises indicator means for indicating the presence of urushiol.

7. A method in accordance with claim 6, wherein said indicator means comprises an alkali selected from the group consisting of sodium and potassium hydroxides and carbonates.

8. A method in accordance with claim 6, wherein said indicator means is selected from the group consisting of ferric nitrate, ferric ammonium citrate, ferric chloride and ferric acetate.

9. A method in accordance with claim 1, wherein said solution further comprises an alkali selected from the group consisting of sodium and potassium hydroxides, bicarbonates, and carbonates.

10. A method in accordance with claim 1, wherein said chlorine-containing compound is selected from the group consisting of chloramine B and chloramine T.

* * * * *